United States Patent [19]

Kuu

[11] Patent Number: 4,518,693
[45] Date of Patent: May 21, 1985

[54] IMMOBILIZED BIOCATALYSTS

[75] Inventor: Wei-Youh Kuu, Baton Rouge, La.

[73] Assignee: Research Corporation, New York, N.Y.

[21] Appl. No.: 437,945

[22] Filed: Nov. 1, 1982

[51] Int. Cl.$^3$ .................. C12N 11/10; C12N 11/04; C12P 7/06

[52] U.S. Cl. .................. 435/178; 435/161; 435/182

[58] Field of Search ............ 435/174, 177, 178, 182, 435/161

[56] References Cited

U.S. PATENT DOCUMENTS

| | | | |
|---|---|---|---|
| 3,849,253 | 11/1974 | Harvey et al. | 435/182 |
| 3,959,251 | 5/1976 | Porath et al. | 435/178 X |
| 4,038,140 | 7/1977 | Jaworek et al. | 435/178 |
| 4,081,329 | 3/1978 | Jaworek et al. | 435/178 |
| 4,138,292 | 2/1979 | Chibata et al. | 435/178 |
| 4,338,401 | 7/1982 | Cremonesi | 435/178 |
| 4,393,136 | 7/1983 | Cheetham | 435/178 X |

FOREIGN PATENT DOCUMENTS 52829 6/1982 European Pat. Off. ............ 435/182

Primary Examiner—David M. Naff
Attorney, Agent, or Firm—Scully, Scott, Murphy & Presser

[57] ABSTRACT

Biocatalysts such as microbial cells are immobilized by forming spherical gel beads containing the microbial cells from a hydrogel such as agar or carrageenan, incubating the beads for a time sufficient to permit the microbial cells to produce $CO_2$ and thereby decrease resistance of the beads to diffusion, diffusing into the beads a monomer, cross-linking agent and accelerator and contacting the beads with a polyermization initiator to cause polymerization of the monomer. The polymerized monomer prevents breakup characteristic of hydrogels containing growing microbial cells. This method is particularly suitable for the immobilization of microbial cells for use in fermentation to produce ethanol.

5 Claims, 1 Drawing Figure

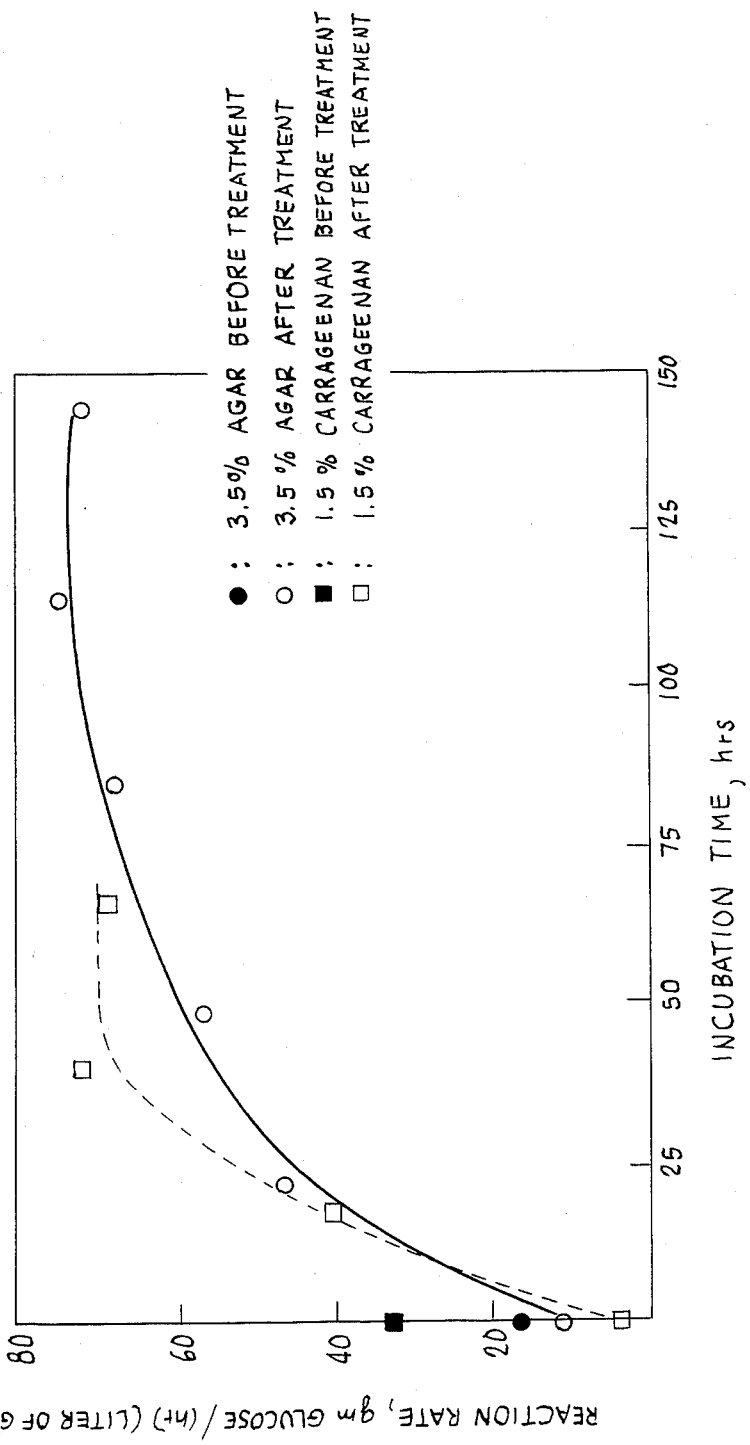

IMMOBILIZED BIOCATALYSTS

BACKGROUND OF THE INVENTION

This invention relates to a method of immobilizing microorganisms. More particularly, this invention is concerned with improvements in the fixing of microbial cells and enzymes on an insoluble support. The immobilized cells may then be used in any of a number of reactions, and the method has been found to be particularly useful for obtaining ethanol by fermentation processes, using immobilized viable cells.

Various techniques have been proposed for immobilizing microbial cells and enzymes on water-insoluble supports. Such methods have included covalent chemical linkage to a support via functional groups of the enzyme that are not essential to enzyme activity, entrapment or inclusion of the enzyme or cell within a hydrophilic gel lattice which retains the enzyme or cell but allows substrate and product to pass through, ionic binding or physical adsorption on hydrophilic ion exchanges or on charcoal or glass beads and cross-linking of the enzymes into large aggregates by reaction with bifunctional compounds.

However, ionic binding has not been uniformly acceptable because partial or total destruction of the enzyme or cell may result from a change in ionic strength, pH or temperature or addition of substrate when a totally insoluble preparation is derived.

Covalent linkage likewise has not provided an acceptable method in that the covalent linkages formed may be broken in use of the immobilized enzyme. Similarly, cross-linking of the enzymes has not been acceptable.

Although presenting the most versatility, entrapment or inclusion presents problems associated with the nature of the hydrophilic gel in which the enzyme or microbial cell is entrapped. That is, the hydrophilic support may be sufficient if used in monolayers, but not be able to withstand packing in a column. Additionally, it may be desirable to form uniform beads of support material with entrapped microbial cells or enzymes, and some supports may be incapable of being formed into beads or into any uniform shape without subjecting the support, with entrapped cells or enzymes, to extremity in temperature.

The immobilization of microbial cells and enzymes by inclusion or entrapment on hydrogels has long been known. However, only a few supports have been reported as successful for ethanol production, such as K-carrageenan and calcium alginate. The reason other supports have been acceptable for ethanol production is that the growth of cells and the production of carbon dioxide within the gel matrix weaken and rupture the gels. Although K-carrageenan and calcium alginate have reasonably high gel strengths which resist rupture, both present other problems. For example, K-carrageenan contains about 20% λ-carrageenan. However, only K-carrageenan has gelling ability. The presence of λ-carrageenan not only reduces the gel strength of the supports but also makes the carrageenan very viscous. Accordingly, crude carrageenan cannot be used for industrial application. Calcium alginate poses problems in that it is unstable in the presence of phosphate buffer and magnesium and potassium ions. Since phosphate salt is a major nutrient for microbial cells, the calcium alginate supports may not be appropriate for anything other than short-term experimentation.

Agar has also been used as a support. The advantage of agar is the fast growth of cells within the gel matrix. However, agar gel is brittle, and its gel strength is reduced by cell growth and the production of carbon dioxide during the initial stage of incubation. After incubation and rapid cell growth, the whole gel becomes very soft and brittle. Accordingly, agar is not suited for industrial applications.

Polyacrylamide has also been used as a support for entrapment of microbial cells and enzymes. Polyacrylamide, however, can only be formed into spherical beads of uniform size with great difficulty. Uniform, spherical bead-shape is a preferred shape.

Additionally, it has been found that ethanol production is drastically lower in those systems which employ polyacrylamide as a support. Accordingly, polyacrylamide gel as a support for entrapment of microbial cells and enzymes has severe use limitations.

SUMMARY OF THE INVENTION

A method of treating hydrogels, such as agar or carrageenan with polyacrylamide, the method resulting in formation of supports for immobilized cells, enzymes, and the like, such supports being rigid, and readily retaining shape after activation of the immobilized cells or enzymes. The method is also useful for immobilizing cells or enzymes on solid substrates such as, but not limited to, glass rods, glass beads, etc. via hydrogels. The treated hydrogels are rigid in the center yet porous in the active layer, i.e., the outer portion of the hydrogel. Microbial cells and enzymes immolutized via this method retain high catalytic activity, and may be used in many systems requiring viable cells, active enzymes, or any other immobilized material. The method is particularly useful in systems employing viable cells for the production of ethanol by fermentation reactions, but is not limited to such application.

DETAILED DESCRIPTION OF THE INVENTION

A polymeric hydrogel, e.g., carrageenan or agar is chosen. The hydrogel is placed in solution, forming a hydrosol, and cell inoculum is added to the hydrogel solution. In a preferred embodiment, the hydrogel is placed in solution at temperatures from 60°-95° C. To form bead shapes, if desired, the mixture of hydrogel and cell inoculum is then dropped into a water immiscible liquid, such as an immiscible oil, the immiscible liquid being at a gel forming temperature below that of the hydrogel solution. The contacting of hydrosol and immiscible liquid results in formation of spherical beads of hydrosol. If the hydrogel selected is carrageenan, the mixture is then dropped into KCl solution to harden the beads. If perfectly spherical beads are desired, and carrageenan is the hydrogel, a two-phase liquid column of paraffin oil on top and KCl solution on the bottom may be used.

The mixture of hydrogel solution and cell inoculum may, additionally, be applied onto solid substrate surfaces. The same procedure for mixing cell inoculum with hydrogel solution as carried out for the production of beads is performed, and a solid substrate surface is introduced to the mixture. The solid surface may be, but is not limited to, any of the following: glass, brick, plastic, or other solid substrate materials. The shape of the solid substrate used may be any which the experimenter desires—for example, glass rods or glass beads.

The immobilized cells are then activated. This, it has been found, aids in decreasing the resistance to diffusion of the first polymer—i.e., the hydrogel. Activation is accomplished by incubating the immobilized cells for anywhere from 12-50 hours in the substrate medium. This is found to produce an active and dense layer of cell colonies, which produces $CO_2$, thereby decreasing hydrogel resistance to diffusion.

Polymerizing monomer cross-linking agent and accelerators are then added to the polymeric beads. These diffuse into the beads, and the amount of diffusion to be expected by the hydrogel may be deduced by noting the diffusion coefficient of each component. One such embodiment of these three components, requires monomer acrylamide (ACAM) (anywhere from 4-15% in solution), N,N'-methylene-bis-acrylamide (BIS) (0.2-0.8% solution), as the cross-linking agent, and either $\beta$-dimethylaminopropionitrile (DMAPN) or N,N,N',N'-tetramethylene-diamine (TEMED) (0.5% solution for either of these) as the accelerator. When placed in a nitrogen sparging container, it has been found that 90% absorption of the slowest diffusing component may be accomplished in 25 minutes, when agar beads (3%, 4 mm) are used as the binding site for the cells. The amount of N,N'-methylene-bis-acrylamide should be kept at 5% (w/w) of the total monomer, for maximum gel strength. Optimum time for diffusion will rely upon both the rate of diffusion into the beads, as well as the toxicity of the diffusing components. Both ACAM and BIS are highly toxic to the immobilized cells, and thus while more of the components will diffuse into the beads when the beads are permitted to remain in the solution for longer intervals, cells will be killed during such longer intervals.

The solution of monomer, cross-linking agent and accelerator molecules is then removed, and the hydrogel beads are contacted with polymerization initiator. This initiator may be, for example $K_2S_2O_8$, or $(NH_4)_2S_2O_8$. The solutions of initiator should be sparged, so as to reduce the concentration of oxygen within the solution. The sparging is necessary, as oxygen is a polymerization inhibitor, and will reduce the desired rate of polymerization unless removed by, for example, sparging with nitrogen gas. In one experiment, 0.5% $K_2S_2O_8$ presparged with nitrogen was used before addition to the gel beads. The initiator is only allowed to remain undisturbed contact the beads for a short time (no more than 3 minutes) so as to prevent excess diffusion of the polymerization components already in the beads. The vessel in which the diffusion is taking place should be covered, so as to prevent any oxygen from entering into the solution and reducing the rate of reaction.

The beads are stirred in the solution, and, it has been found that for 4 mm 3% agar beads, 30 minutes of stirring will permit greater than 90% absorption of the initiator. The rate of polymerization may be observed by monitoring the change of temperature within the beads. As the zone of polymerization, moves slowly from the outer layer to the inner layer, the temperature of the beads will rise only slightly. Heat deactivation of the live cells is thus minimized.

Following this treatment, the beads are washed so as to eliminate unpolymerized components. The polymerized ACAM molecules (polyacrylamide), by this process, have been cross-linked to the polymer molecules of the hydrogel. The result is a bead array with much higher gel strength than previously observed, with the size and shape of the beads remaining unchanged after polymerization.

The resulting bond, or entrapped cultures, may then be used in processes wherein the particular culture produces a useful or desired product. Those skilled in the art will readily see that any reaction or series of reactions which depends upon an immobilized cell culture, enzyme culture, or the like, may benefit from the use of this invention. One particular use of this invention's usefulness may be seen in its application to processes for the production of ethanol by fermentation, such fermentation brought about by the action of yeast cells. Yeast cells are bound to polymeric hydrogels via methods described herein. Following such binding, the hydrogel-cell complexes are placed in fermentation broth. The fermentation broth may be of varied composition, as long as at least one source of nourishment (e.g., glucose) is provided within the broth.

The accompanying figure, as well as Example 6, shows the usefulness of this method in the production of ethanol. Experimental runs were performed, using immobilized yeast cells on carrageenan and agar gels, both with and without polymerization treatment. Reaction rate is plotted as a measure of the amount of glucose, in grams, used by immobilized yeast cells per hour per liter of gel used, against the incubation time, in hours. For both agar and carrageenan, the reaction rate, while static for untreated gel, rises exponentially until maximum rate is achieved, when treated for polymerization.

EXAMPLE 1

Rate of polymerization of acrylamide under various conditions is to be determined. This is established by comparing the rise in temperature at the center of polymerizing mixtures.

A solution of monomer acrylamide (ACAM), N,N'-methylene-bis-acrylamide (BIS), and either the accelerator B-dimethyl-aminopropionitrile (DMAPN) or N,N,N',N'-tetramethylexediamine (TEMED) is sparged with pressurized nitrogen for 15-30 minutes, in an Erlenmeyer flask, with a thermometer at the center of the liquid. A second vessel contains a solution of either $K_2S_2O_8$ or $(NH_4)_2S_2O_8$, which is also sparged with nitrogen for 15-30 minutes.

The second solution is poured into the first solution, and nitrogen sparging is continued. Temperature rise vs. time was recorded. The polymerization reaction eventually stops the sparging nitrogen. The time at which this occurs is referred to as the "initial starting time" as set out in Table 1. It is found that rapid polymerization with the formation of clear gels occurs at room temperature of higher, with concentrations of DMAPN or TEMED of 0.5% w/v or higher.

EXAMPLE 2

Mechanical strengths of various gels are tested. So that a uniform standard for comparison could be obtained, all gels were cast in a 5.85 cm diameter disk, 2 mm thick. Carrageenan gels were treated with 1% KCl solution prior to gel phase polymerization (GPP). No microbial cells were introduced to the system and the ACAM, BIS, DMAPN or TEMED solution was permitted to diffuse for 2 hours, the same amount of time allocated to the $K_2S_2O_8$ or $(NH_4)_2S_2O_8$ reaction. Gel strength was then defined as the force required to rupture the specimen by cutting through the gel with Instron Universal Testing Instrument, Model 1122 (serial no. 4687). The results of these experiments set forth in Table 2, show, for example, that the gel strength of 3.5% agar gel, after polymerizing with 15% ACAM and 0.8 BIS is 2.8 times that of the gel without such treatment.

EXAMPLE 3

The effect of oxygen on GPP was tested. A gel of 3.5% agar was treated for GPP but without sparging by nitrogen. Results showed a gel strength of 0.357 kg/cm², far lower than that obtained with nitrogen sparging 0.592 kg/cm².

EXAMPLE 4

The strength of 3.5% agar gel, obtained by adding ACAM, BIS and DMAPN to the agar solution directly, rather than preparing two separate solutions and mixing, was also determined. Gel strength was found to be 0.580 kg/cm², very close to that obtained by using two distinct solutions, i.e., 0.592 kg/cm².

EXAMPLE 5

The strength of 1.5% carrageenan gel was also tested. The gel was treated with 15% ACAM and 0.8% BIS, under conditions identical to those in Example 2. The gel strength, as set out in Table 2, is approximately much higher than no-treated carrageenan as treated 3.5% agar gel is higher than non-treated agar gel (2.68 kg/cm² as compared to 0.95 kg/cm²).

EXAMPLE 6

Catalytic activation of microbial cells after GPP was determined. 41 ml of treated 3.5% agar beads of average diameter 3.98 mm, and 40 ml of treated 1.5% carrageenan beads of average diameter 3.86 mm were placed in separate magnetic stirring reactors, filled with 3% glucose complete medium. Treatment was carried out with a medium of 7.5% ACAM, 0.4% BIS, 0.5% DMAPN, and 0.5% $K_2S_2O_8$. Activation was measured by monitoring by measuring ethanol produced vs. incubation time. This may be expressed by grams of glucose converted per hour per liter, and is plotted in the accompanying figure, wherein the reaction rate, in terms of grams of glucose produced per hour per liter of gel, is plotted against incubation time, in hours. Results show that activation proceeded rapidly after GPP treatment, with saturated activity attained after about 90 hours of incubation with 3.5% agar gel, and as little as 35 hours for 1.5% carrageenan gel.

The actual maximum productivity was calculated for 3.5% agar gel as 37.82 g of ethanol/hr./liter of gel and 35.78 g of ethanol/hr./liter of gel for 1.5% carrageenan after GPP treatment. Maximum activity of treated 3.5% agar is 4.35 times that without treatment at 29.7 hours after incubation. Comparably, the maximum activity of treated 1.5% carrageenan gel, after 51 hours of incubation, is 2.5 times that without treatment.

TABLE I

The Initial Setting Time of Polyacrylamide Under Various Polymerization Conditions.

| Polymerization Conditions[a] | | | | | Initial Setting Time (Sec.) | Type of Gel |
|---|---|---|---|---|---|---|
| Final DMAPN % | Final TEMED % | Final $K_2S_2O_8$ % | Final $(NH_4)_2S_2O_8$ | Initial Temp (°C.) | | |
| 0.5 | | 0.5 | | 23 | 10 | clear |
| 0.5 | | | 0.42[b] | 1 | 40 | cloudy |
| | 0.5 | | 0.42 | 1 | 40 | cloudy |
| | 0.5 | | 0.42 | 23 | 10 | clear |

[a]The final concentration of the other components are: 7.5% ACAM, and 0.4% BIS.
[b]0.42% $(NH_4)_2S_2O_8$ is equivalent to 0.5 $K_2S_2O_8$ in molar basis. At low temperature $K_2S_2O_8$ was replaced by $(NH_4)_2S_2O_8$ because of its limited solubility.

TABLE II

The Shear Breaking Strength of Various Gels*

| Type of Gel | Polymerization Condition | | Gel Strength kg/cm² × 10 | Remark |
|---|---|---|---|---|
| | % ACAM | % BIS | | |
| | 0.0 | 0.0 | 2.12 | |
| | 7.5 | 0.4 | 5.17 | |
| 3.5% | 15.0 | 0.8 | 5.92 | No $N_2$ sparge |
| Agar | 7.5 | 0.4 | 2.6 | No $N_2$ sparge |
| | 15.0 | 0.8 | 3.57 | Direct inclusion of ACAM |
| | 15.0 | 0.8 | 5.80 | BIS and DMAPN |
| 1.5% | 0.0 | 0.0 | 0.95 | |
| Carrageenan | 7.5 | 0.4 | 2.16 | |
| | 15.0 | 0.8 | 2.68 | |
| Polyacrylamide | 7.5 | 0.4 | 1.42 | |
| | 15.0 | 0.8 | 1.60 | |

*Size of specimens: 5.85 cm in diameter and 2 mm in thickness.

What is claimed is:

1. A method for immobilization of microbial cells comprising:
    (a) forming a solution of an agar or carrageenan hydrogel;
    (b) introducing microbial cells into the hydrogel solution, said microbial cells being at temperature 40°-48° C. when agar is used, and 37°-50° C. when ccarrageenan is used;
    (c) forming spherical gel beads of the microbial cell containing hydrogel solution, such beads created by contacting the hydrogel solution with a water-immiscible liquid at a temperature below that of the hydrogel solution;
    (d) activating the microbial cells by incubating the spherical beads containing culture for 12–50 hours, such incubation resulting in the formation of colonies of microbial cells in the spherical beads which produce $CO_2$ thereby decreasing resistance of the beads to diffusion;
    (e) diffusing the monomer, acrylamide (ACAM), the cross-linking agent, N,N'-methylene-bis-acrylamide (BIS), and the accelerator, β-dimethylaminopropionitrile (DMAPN) or N,N,N',N'-tetramethylenediamine (TEMED) into the beads by introducing the ACAM, BIS, and DMAPN or TEMED to the gel beads in solution;
    (f) after diffusion removing the solution of ACAM, BIS and either DMAPN or TEMED;
    (g) contacting the gel beads with a polymerization initiator selected from the group consisting of $K_2S_2O_8$ and $(NH_4)_2S_2O_8$ to cause polymerization;

(h) sparging the solution with nitrogen during polymerization;
(i) stirring the beads so as to increase uptake of polymerization initiator, and;
(j) washing the polymerized beads with water to remove unpolymerized molecules.

2. The method of claim 1 wherein ACAM is present in solution from 4 to 15%.

3. The method of claim 1 wherein BIS is present in solution from 0.2 to 0.8%.

4. The method of claim 1 wherein DMAPN and TEMED are present in solution at about 0.5%.

5. A method for the production of ethanol by fermentation comprising employing spherical beads containing microbial cells produced by the method of claim 1.

* * * * *